United States Patent
Kopetsch et al.

(10) Patent No.: US 8,629,191 B2
(45) Date of Patent: Jan. 14, 2014

(54) PROCESS AND PLANT FOR PRODUCING METHANOL

(75) Inventors: Hans Kopetsch, Bad Homburg (DE); Philipp Marius Hackel, Usingen (DE); Veronika Gronemann, Karben (DE); Rainer Morgenroth, Friedrichsdorf (DE)

(73) Assignee: Lurgi GmbH, Frankfurt am Main (DE)

( * ) Notice: Subject to any disclaimer, the term of this patent is extended or adjusted under 35 U.S.C. 154(b) by 316 days.

(21) Appl. No.: 13/121,562

(22) PCT Filed: Jul. 29, 2009

(86) PCT No.: PCT/EP2009/005483
§ 371 (c)(1),
(2), (4) Date: Mar. 29, 2011

(87) PCT Pub. No.: WO2010/037440
PCT Pub. Date: Apr. 8, 2010

(65) Prior Publication Data
US 2011/0178188 A1    Jul. 21, 2011

(30) Foreign Application Priority Data
Sep. 30, 2008 (DE) .......... 10 2008 049 621

(51) Int. Cl.
*C07C 27/00* (2006.01)
(52) U.S. Cl.
USPC ............. 518/706; 518/700; 518/705
(58) Field of Classification Search
USPC ........................ 518/700, 705, 706
See application file for complete search history.

(56) References Cited

U.S. PATENT DOCUMENTS

| 3,516,800 | A | 6/1970 | Yamamoto et al. |
| 5,827,901 | A | 10/1998 | König et al. |
| 7,144,923 | B2 | 12/2006 | Fitzpatrick |
| 2006/0074133 | A1* | 4/2006 | Fitzpatrick ............... 518/726 |

FOREIGN PATENT DOCUMENTS

GB    1604980    12/1981

OTHER PUBLICATIONS

PCT Notification Concerning Transmittal of International Preliminary Report on Patentability from International Application No. PCT/EP2009/005483, corresponding to U.S. Appl. No. 13/121,562, mailed Apr. 14, 2011, pp. 1-9.
PCT International Search Report from International Application PCT/EP2009/005483, mailed Nov. 9, 2009, 2 pages.
Baerns, M. et al., Organische Zwischenprodukte (Organic Between Products), *Technische Chemie*, (*Technical Chemistry*), with English translation, vol. 17, p. 560, 2006 (5 pages).

* cited by examiner

*Primary Examiner* — Jafar Parsa
(74) *Attorney, Agent, or Firm* — Pauly, Devries Smith & Deffner, L.L.C.

(57) ABSTRACT

For producing methanol from a synthesis gas containing hydrogen and carbon oxides the synthesis gas is passed through a first, water-cooled reactor in which a part of the carbon oxides is catalytically converted to methanol. The resulting mixture containing synthesis gas and methanol vapor is supplied to a second, gas-cooled reactor in which a further part of the carbon oxides is converted to methanol. Subsequently, methanol is separated from the synthesis gas, and synthesis gas is recirculated to the first reactor. The cooling gas flows through the second reactor cocurrent to the mixture withdrawn from the first reactor.

5 Claims, 2 Drawing Sheets

PROCESS AND PLANT FOR PRODUCING METHANOL

CROSS-REFERENCE TO RELATED APPLICATIONS

This application is a national stage application under 35 U.S.C. 371 of International Patent Application Serial No. PCT/EP2009/005483, entitled "Process and Plant for Producing Methanol," filed Jul. 29, 2009, which claims priority from German Patent Application No. 10 2008 049 621.9, filed Sep. 30, 2008.

FIELD OF THE INVENTION

This invention relates to the production of methanol from a synthesis gas containing hydrogen and carbon oxides, wherein the synthesis gas is passed through a first, water-cooled reactor in which a part of the carbon oxides is catalytically converted to methanol, wherein the resulting mixture containing synthesis gas and methanol vapor is supplied to a second, gas-cooled reactor in which a further part of the carbon oxides is catalytically converted to methanol, wherein methanol is separated from the synthesis gas and wherein synthesis gas is recirculated to the first reactor.

BACKGROUND OF THE INVENTION

Processes for producing methanol are known for example from EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper catalyst. The methanol produced in the process is separated from the synthesis gas to be recirculated, which then is countercurrently passed through the gas-cooled reactor as coolant and preheated to a temperature of 220 to 280° C., before it is introduced into the first synthesis reactor. In the case of unsteady plant conditions and in particular in the case of an improper start-up of the reactor by too early addition of fresh synthesis gas, this procedure can, however, lead to a condensation of the methanol product in the gas-cooled second reactor, since the reactor wall temperature at the outlet can approach the dew point of the product gas.

From U.S. Pat. No. 7,144,923 B2 a process for methanol synthesis is known, in which the synthesis gas first passes through an adiabatic reactor stage, in which a part of the synthesis gas is converted to methanol, and subsequently is supplied to a gas-cooled reactor for further conversion. The gas entering the gas-cooled reactor is guided cocurrent to the fresh gas, in order to achieve a better temperature control of the synthesis gas and a better heat recovery. When using an adiabatic first reactor, however, the CO content of the usable synthesis gas is restricted, since the control of the exotherm in the first reactor can create problems. In addition, it is required to perform cooling of the partly converted synthesis gas after each stage of the first reactor, which complicates the design of the reactor.

SUMMARY OF THE INVENTION

It is the object of the invention to reliably avoid the condensation of methanol at the outlet of the gas-cooled second reactor in particular when using a water-cooled first reactor.

This object substantially is solved with the invention in that the cooling gas flows through the second reactor cocurrent to the mixture withdrawn from the first reactor. The distance of the product temperature from the dew point at the lower end of the reactor thereby is increased, so that a methanol condensation largely is excluded. By avoiding a two-phase flow, an improved reactor control can also be achieved. At the same time, pressure losses and/or fluctuations of the reactor pressure can reliably be avoided.

Since the use of a water-cooled first reactor provides for using a "sharper" synthesis gas with higher CO contents than in an adiabatic reactor according to U.S. Pat. No. 7,144,923 B2, the conversions can be increased and a higher concentration of methanol and water as coupling product in the product gas can be achieved after the first reactor. This leads to a higher dew point, so that avoiding condensation in the second reactor becomes even more important.

In accordance with a preferred aspect of the process it is provided that as cooling gas for the second reactor synthesis gas is used, which has been separated from the mixture withdrawn from the second reactor. In this way, a maximum utilization of the heat obtained by the exothermal reaction process can be achieved.

In accordance with the invention, the cooling gas is introduced into the second reactor with a temperature of 100 to 120° C. and withdrawn from the same with a temperature of 205 to 215° C.

In accordance with a development of the invention, the cooling gas withdrawn from the second reactor then is recirculated to the first reactor, wherein the recirculated cooling gas is supplied to the first reactor together with fresh synthesis gas and the content of fresh synthesis gas preferably is about 15 to 40 vol-%.

The invention also extends to a plant for producing methanol from a synthesis gas containing hydrogen and carbon oxides, which is suitable for performing the process described above. The plant comprises a first, water-cooled reactor in which a part of the carbon oxides is catalytically converted to methanol, a second, gas-cooled reactor to which the gas mixture obtained from the first reactor is supplied via a conduit and in which a further part of the carbon oxides is converted to methanol, a separating means for separating the methanol from the synthesis gas, and a return conduit for recirculating synthesis gas to the first reactor. In accordance with the invention, a cooling conduit extends from the separating means to the inlet of the second reactor, via which synthesis gas is supplied to the second reactor such that the synthesis gas flows through the second reactor cocurrent to the gas mixture obtained from the first reactor.

Further developments, advantages and possible applications of the invention can also be taken from the following description of an embodiment and the drawing. All features described and/or illustrated form the subject-matter of the invention per se or in any combination, independent of their inclusion in the claims or their back-reference.

DETAILED DESCRIPTION

Figure 1:
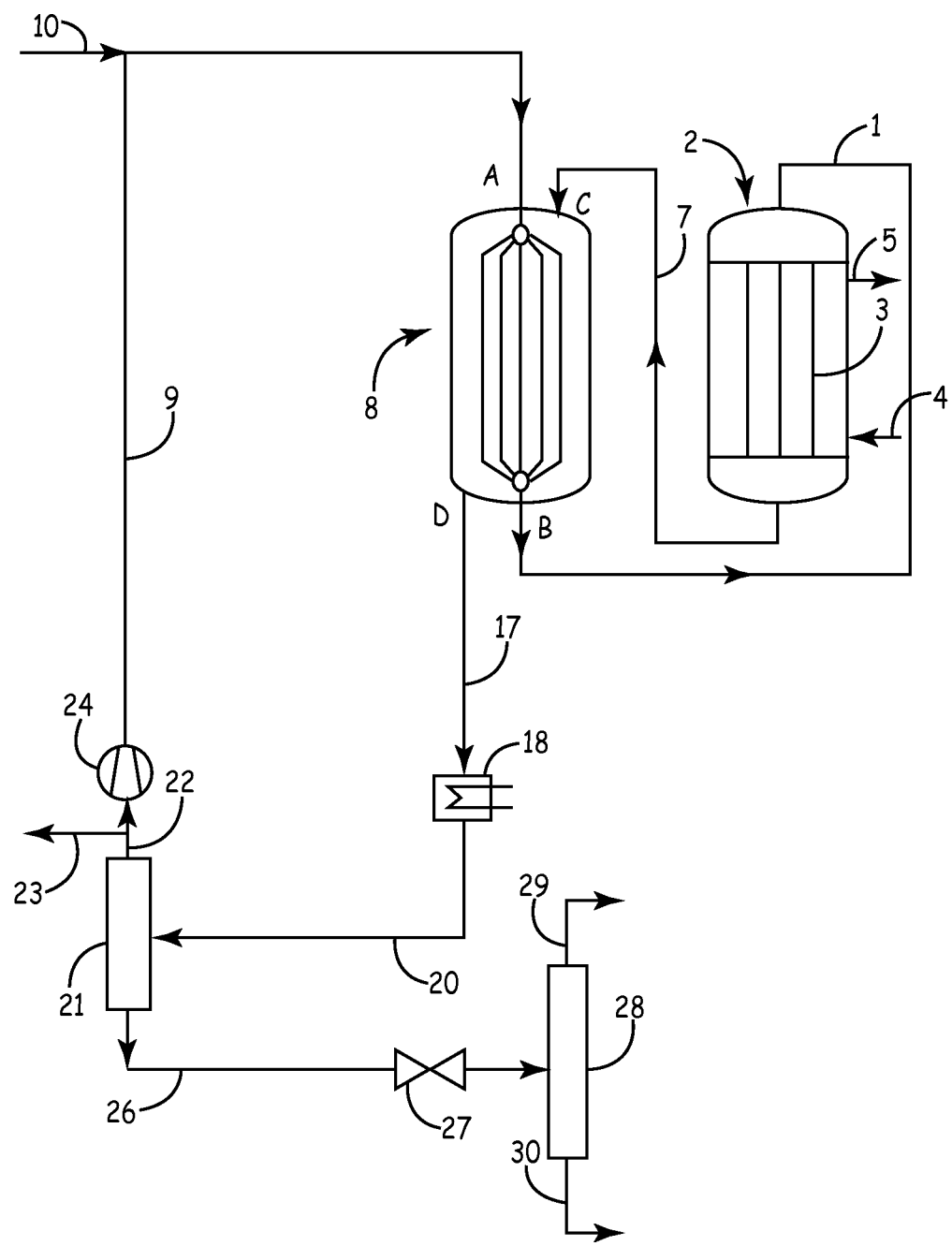
FIG. 1 schematically shows a plant for performing the process of the invention.

In the plant shown in FIG. 1, a mixture of fresh and recirculated synthesis gas is passed through a conduit 1 into a first synthesis reactor 2. This first reactor 2 for example is a tubular reactor known per se, in which for example a copper catalyst is arranged in tubes 3. As coolant, water boiling under elevated pressure is used, which is supplied in conduit 4. A mixture of boiling water and steam is withdrawn in conduit 5 and supplied to a non-illustrated steam drum known per se for energy recovery.

The synthesis gas entering the first reactor 2 is preheated to a temperature>220° C., since the catalyst will only respond from this temperature. Usually, the gas temperature at the inlet of the first reactor 2 is about 220 to 280° C. and the pressure lies in the range from 2 to 12 MPa (20 to 120 bar), preferably in the range from 4 to 10 MPa (40 to 100 bar). The coolant which is withdrawn via conduit 5 usually has a temperature in the range from 240 to 280° C. Depending on the condition of the catalyst, 40 to 80% of the carbon oxides charged to the reactor 2 through conduit 1 are converted in an exothermal reaction in the first reactor 2.

From the first reactor 2, a first mixture substantially consisting of synthesis gas and methanol vapor is withdrawn via conduit 7, wherein the methanol content is 4 to 10 vol-%, mostly 5 to 8 vol-%. This mixture is introduced into the second synthesis reactor 8, which for example likewise is configured as a tubular reactor with a copper catalyst. As in the first reactor 2, the catalyst can be provided in the tubes or preferably on the shell side.

In the second reactor 8, synthesis gas is used as cooling medium, which is supplied via conduit 9 with a temperature of 80 to 130° C. and flows through the second reactor 8 cocurrent to the first mixture coming from the first reactor 2.

Fresh synthesis gas, which is generated in a non-illustrated plant known per se, is supplied in conduit 10 and admixed to the synthesis gas to be recirculated. The temperature of the cooling gas at the inlet of the second reactor 8 results from the mixing ratio between recirculated and fresh synthesis gas and is chosen the lower the higher the inlet temperature of the first mixture flowing into the second reactor 8. The synthesis gas used as coolant is preheated in the second reactor 8 and then flows through the conduit 1 to the first reactor 2.

The synthesis gas which enters the first reactor 2 should include hydrogen and carbon oxides approximately in the following proportions:
$H_2$=40 to 80 vol-%
CO=3 to 15 vol-% and
$CO_2$=1 to 10 vol-%.

A product mixture substantially containing synthesis gas and methanol vapor (second mixture) leaves the second reactor 8 through a conduit 17 and flows through an indirect cooler 18, whereby methanol is condensed. Subsequently, the mixture is charged through conduit 20 into a first separation tank 21, in which gases and liquid are separated. The gases are withdrawn through conduit 22, wherein a part can be removed from the process via a conduit 23. By means of the condenser 24, the gases are passed as synthesis gas to be recirculated (recycle gas) via conduit 9 through the second reactor 8 and are passed on into the first reactor 2 after the resulting preheating.

From the first separation tank 21, liquid containing methanol is withdrawn via a conduit 26, and the liquid is passed through an expansion valve 27 to a second separation tank 28. From said tank, a residual gas is withdrawn via a conduit 29, whereas via conduit 30 crude methanol is obtained, which now is purified by distillation in a non-illustrated manner known per se.

It should be appreciated that the design of the reactors 2, 8 as such is not limited to the variants described above. Rather, modifications of these reactors are also possible, for example as described in EP 0 790 226 B1.

Figure 2:
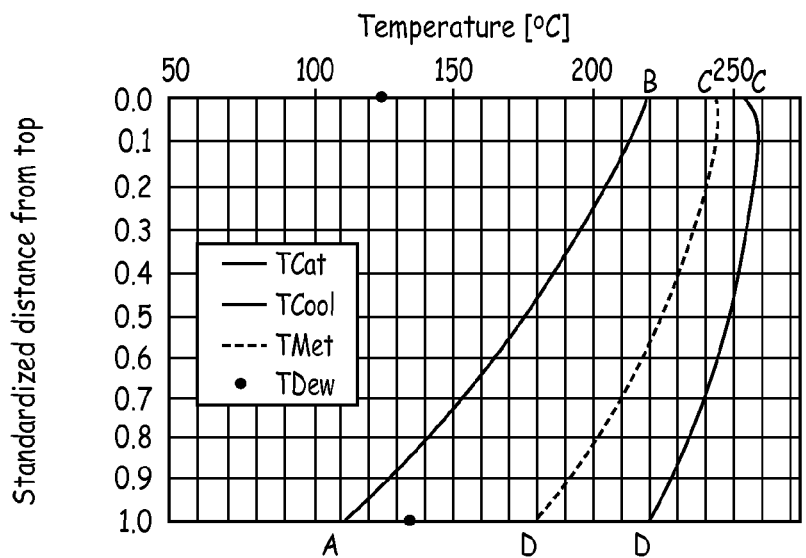
FIG. 2 shows the temperature profile of various reactor components along the standardized length of the gas-cooled reactor for countercurrently guided cooling gas.
Figure 3:
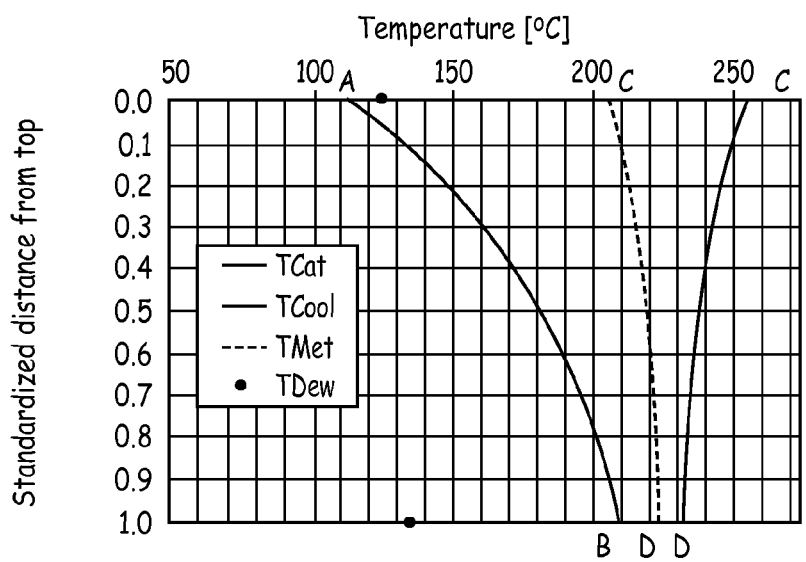
FIG. 3 shows the temperature profile of various reactor components along the standardized length of the gas-cooled reactor for cocurrently guided cooling gas.

In the diagrams as shown in FIG. 2 and FIG. 3, the temperature profiles of the catalyst (TCat), of the cooling gas (TCool) and of the cooling tube wall (TMet) along the standardized reactor length are illustrated by way of example for a cooling gas guided countercurrent to the first mixture coming from the first reactor 2 (FIG. 2, cf. EP 0 790 226 B1) and for a cooling gas guided cocurrent to the first mixture coming from the first reactor 2 (FIG. 3), respectively, in accordance with the present invention. The starting and end points of the temperature curves designate the following points in the second reactor:

A: entry cooling gas
B: exit cooling gas
C: entry first mixture (reaction gas)
D: exit second mixture (reaction gas)

TDew designates the dew point of the product mixture at the inlet and outlet of the second reactor, which rises with the methanol concentration.

In the illustrated example, the following process data are obtained:

|  | Countercurrent Flow (EP 0 790 226 B1) | Cocurrent Flow (invention) |
| --- | --- | --- |
| Cooling gas in (A) [° C.] | 112 | 112 |
| Cooling gas out (B) [° C.] | 218 | 209 |
| Reaction gas in (C) [° C.] | 255 | 255 |
| Reaction gas out (D) [° C.] | 220 | 233 |
| Distance dew point, top [° C.] | 117 | 81 |
| Distance dew point, bottom [° C.] | 45 | 86 |

In normal operation, the distance between the dew point TDew of the reaction gas and the temperature of the cooling tube wall TMet at the coldest point in the lower part of the reactor amounts to some 10° C. In the case of an improper start-up of the reactors due to too early addition of fresh synthesis gas into the cycle, this safe distance (45° C.) can get lost in the case of a countercurrent flow and a condensation of the reaction gas can occur.

In the case of a cocurrent flow, on the other hand, the distance of the temperature of the cooling tube wall TMet from the dew point of the product mixture TDew is almost doubled to 86° C. in the critical region (exit of the product mixture) as compared to the countercurrent flow. Even when restarting the synthesis cycle with tempered reactors after a brief shutdown of the plant, the risk of a condensation due to too early addition of synthesis gas hence is considerably lower.

In addition, a flatter temperature curve is obtained along the reactor length with lower peak temperatures. This is advantageous for the runtime stability of the catalyst.

Figure 4:
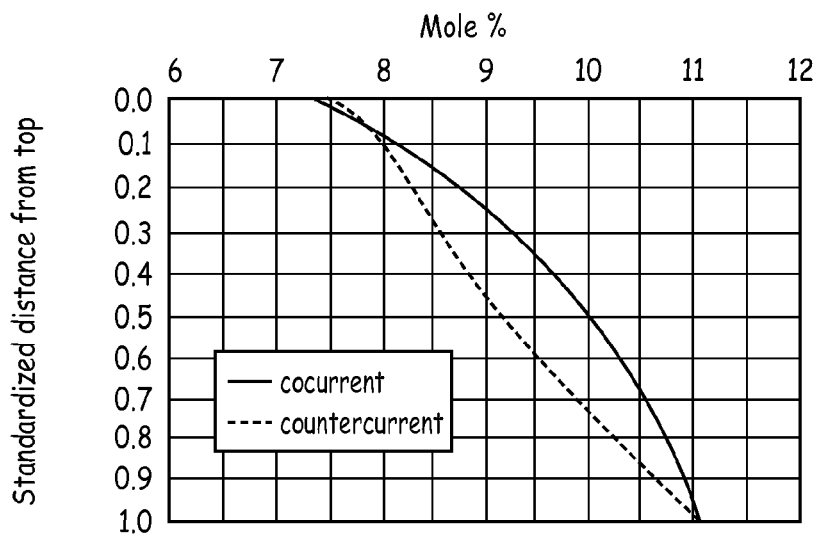
FIG. 4 shows the course of the methanol content along the standardized reactor length for cocurrently and countercurrently guided cooling gas.

FIG. 4 shows the rise of the methanol content along the reactor length for cocurrently and countercurrently guided cooling gas. It can be seen that both concepts approximately yield the same total production. Due to the flatter temperature profile, however, the cocurrent flow provides more methanol on the first ⅔ of the reactor length than the countercurrent flow.

LIST OF REFERENCE NUMERALS 1 conduit
2 first reactor
3 tubes
4 conduit
5 conduit
7 conduit
8 second reactor
9 conduit
10 conduit
17 conduit
18 cooler
20 conduit
21 separation tank
22 conduit
23 conduit
24 compressor
26 conduit
27 expansion valve
28 second separation tank
29 conduit
30 conduit
A entry cooling gas
B exit cooling gas
C entry first mixture (reaction gas)
D exit second mixture (reaction gas)

The invention claimed is:

1. A process for producing methanol from a synthesis gas containing hydrogen and carbon oxides, wherein the synthesis gas is passed through a first, water-cooled reactor in which a part of the carbon oxides is catalytically converted to methanol, wherein the resulting mixture containing synthesis gas and methanol vapor is supplied to a second, gas-cooled reactor in which a further part of the carbon oxides is converted to methanol, wherein methanol is separated from the synthesis gas and wherein synthesis gas is recirculated to the first reactor, wherein the cooling gas flows through the second reactor cocurrent to the mixture withdrawn from the first reactor; wherein the cooling gas is introduced into the second reactor with a temperature of 100 to 120° C.

2. The process according to claim 1, wherein as cooling gas for the second reactor synthesis gas is used, which has been separated from the mixture withdrawn from the second reactor.

3. The process according to claim 1, wherein the cooling gas is withdrawn from the second reactor with a temperature of 205 to 215° C.

4. The process according to claim 1, wherein the cooling gas withdrawn from the second reactor is recirculated to the first reactor.

5. The process according to claim 1, wherein the recirculated cooling gas is supplied to the first reactor together with fresh synthesis gas and that the content of fresh synthesis gas is about 15 to 40 vol-%.

* * * * *